US008383783B2

(12) United States Patent
Lees et al.

(10) Patent No.: US 8,383,783 B2
(45) Date of Patent: Feb. 26, 2013

(54) SIMPLE METHOD FOR SIMULTANEOUS REMOVAL OF MULTIPLE IMPURITIES FROM CULTURE SUPERNATANTS TO ULTRALOW LEVELS

(75) Inventors: Andrew Lees, Silver Spring, MD (US); Jayant Sakaram Joshi, Pune (IN)

(73) Assignees: Serum Institute of India, Ltd., Pune (IN); Fina BioSolutions, LLC, Rockville, MD (US)

( * ) Notice: Subject to any disclaimer, the term of this patent is extended or adjusted under 35 U.S.C. 154(b) by 123 days.

(21) Appl. No.: 12/973,455

(22) Filed: Dec. 20, 2010

(65) Prior Publication Data

US 2011/0263834 A1   Oct. 27, 2011

Related U.S. Application Data

(60) Provisional application No. 61/327,238, filed on Apr. 23, 2010.

(51) Int. Cl.
*C07K 1/16* (2006.01)

(52) U.S. Cl. ........................................ 530/417

(58) Field of Classification Search ........................ None
See application file for complete search history.

(56) References Cited

U.S. PATENT DOCUMENTS

| | | |
|---|---|---|
| 4,356,170 A | 10/1982 | Jennings et al. |
| 4,540,573 A | 9/1985 | Neurath et al. |
| 4,678,553 A | 7/1987 | Mandle et al. |
| 4,695,624 A | 9/1987 | Marburg et al. |
| 5,039,607 A | 8/1991 | Skold et al. |
| 5,306,492 A | 4/1994 | Porro |
| 5,360,897 A | 11/1994 | Anderson et al. |
| 5,425,946 A | 6/1995 | Tai et al. |
| 5,585,100 A | 12/1996 | Mond et al. |
| 5,651,971 A | 7/1997 | Lees |
| 5,681,570 A | 10/1997 | Yang et al. |
| 5,693,326 A | 12/1997 | Lees |
| 5,747,663 A | 5/1998 | Colpan et al. |
| 5,849,301 A | 12/1998 | Lees |
| 5,955,079 A | 9/1999 | Mond et al. |
| 6,087,328 A | 7/2000 | Lees |
| 6,146,902 A | 11/2000 | McMaster |
| 6,248,334 B1 | 6/2001 | Lees et al. |
| 6,284,250 B1 | 9/2001 | Lees et al. |
| 6,299,881 B1 | 10/2001 | Lees et al. |
| 6,309,646 B1 | 10/2001 | Lees |
| 6,428,703 B1 | 8/2002 | Zinn et al. |
| 6,432,679 B1 | 8/2002 | Mond et al. |
| 6,585,973 B1 | 7/2003 | Lees |
| 6,596,172 B1 | 7/2003 | Kopf |
| 6,756,041 B2 | 6/2004 | Lees et al. |
| 6,765,091 B1 | 7/2004 | Bencomo et al. |
| 7,094,883 B1 | 8/2006 | Cassels et al. |
| 7,101,562 B1 | 9/2006 | Lees et al. |
| 7,166,708 B2 | 1/2007 | Lees et al. |
| 7,250,494 B2 | 7/2007 | Stinson et al. |
| 7,452,533 B2 | 11/2008 | Walsh et al. |
| 7,470,441 B2 | 12/2008 | Van Der Giessen et al. |
| 7,566,540 B2 | 7/2009 | Cassels et al. |
| 7,777,017 B2 | 8/2010 | Stinson et al. |
| 2002/0054879 A1 | 5/2002 | Lees et al. |
| 2002/0119529 A1 | 8/2002 | Mond et al. |
| 2003/0215436 A1 | 11/2003 | Walsh et al. |
| 2003/0224000 A1 | 12/2003 | Kokai-Kun et al. |
| 2003/0235578 A1 | 12/2003 | Stinson et al. |
| 2004/0052779 A1 | 3/2004 | Stinson et al. |
| 2005/0074460 A1 | 4/2005 | Lees et al. |
| 2005/0075486 A1 | 4/2005 | Cassels et al. |
| 2005/0169941 A1 | 8/2005 | Lees |
| 2005/0222434 A1 | 10/2005 | Bessodes et al. |
| 2006/0165822 A1 | 7/2006 | Van Der Giessen et al. |
| 2007/0065465 A1 | 3/2007 | Lees et al. |
| 2007/0292404 A1 | 12/2007 | Walsh et al. |
| 2008/0019976 A1 | 1/2008 | Stinson et al. |
| 2009/0081180 A1 | 3/2009 | Walsh et al. |
| 2011/0263834 A1 | 10/2011 | Lees et al. |

FOREIGN PATENT DOCUMENTS

| | | |
|---|---|---|
| WO | WO9521177 | 8/1995 |
| WO | WO9521179 | 8/1995 |
| WO | WO96/17941 | 6/1996 |
| WO | WO96/40662 | 12/1996 |
| WO | WO01/70685 | 9/2001 |
| WO | WO03/057849 | 7/2003 |
| WO | WO03/097699 | 11/2003 |
| WO | WO2004104811 | 12/2004 |
| WO | WO2005/056608 | 6/2005 |
| WO | WO2006-032475 | 3/2006 |

(Continued)

OTHER PUBLICATIONS

Keefe et al. (Nature, 410:715-718 and supplemental materials, accessed at http://www.nature.com/nature/journal/v410/n6829/extref/410715a0_S1.htm, 2001).*

(Continued)

*Primary Examiner* — Brian J Gangle
(74) *Attorney, Agent, or Firm* — Remenick PLLC

(57) ABSTRACT

This invention is directed to methods for removing, preferably simultaneously and in one step, multiple impurities form crude culture samples, and, in particular, the removal of media components, protein, nucleic acids, lipids, and lipopolysaccharides to ultralow levels. Preferably the purification process comprises: (1) binding of the target substance containing one or more contaminants to a chromatography matrix; (2) washing the bound target substance with one or more buffers containing a synergistic combination of a lyotropic agent or organic solvent, a detergent, and a salt component; and (3) desorbing the target substance from the chromatography matrix, so that the eluate contains ultra low levels of contaminants. The reduction of impurities that can be achieved is preferably 91-99.9% as compared to the amount of impurities in the target substance before purification. The invention is also directed to the targets products that have been so purified.

36 Claims, No Drawings

FOREIGN PATENT DOCUMENTS

WO     WO2008-021076     2/2008

OTHER PUBLICATIONS

PCT Search Report for PCT/US10/61313, dated Feb. 15, 2011.
PCT Patentability Report for PCT/US10/61313, dated Feb. 15, 2011.
PCT Patentability Report for PCT/US2010/055107, dated May 8, 2012.
Chinese Office Action for Chinese application No. 200580010225.4, dated May 18, 2012.
PCT Patentability Report for PCT/US2010/043387, dated Apr. 27, 2011.
D. C. Watson, J. B. Robbins, and S. C. Szu, "Protection of mice against *Salmonella typhimurium* with an O-specific polysaccharide-protein conjugate vaccine," Infection and Immunity 60:4679-4686, 1992.
Konadu, J. Shiloach, D. A. Bryla, J. B. Robbins, and S. C. Szu, "Synthesis, characterization, and immunological properties in mice of conjugates composed of detoxified lipopolysaccharide of *Salmonella paratyphi* a bound to tetanus toxoid, with emphasis on the role of O-acetyls," Infect Immun. Jul. 1996; 64(7):2709-15.
Schneerson R, Barrera O, Sutton A, Robbins JB. Preparation, characterization, and immunogenicity of *Haemophilus influenzae* type b polysaccharide-protein conjugates. J Exp Med. Aug. 1, 1980;152(2):361-376.
PCT Search Report for PCT/US2010/043387, dated Apr. 27, 2011.
Chu, et al., "Further studies on the immunogenicity of *Haemophilus influenzae* type b and pneumococcal type 6A polysaccharide-protein conjugates," Inf. & Imm., 40:245-256 (1983).
Jennings, et al., "Conjugation of meningococcal lipopolysaccharide R-type oligosaccharides to tetanus toxoid as a route to a potential vaccine against group B *Neisseria meningitides*," Inf. & Immun., 43:407-412 (1984).
Laferriere et al., "The Synthesis of *Streptococcus pneumoniae* polysaccharide-tetanus toxoid conjugates and the effect of chain length on immunogenicity," Vaccine, 15:179 (1997).
Kohler, et al., "Continuous cultures of fused cells secreting antibody of predefined specificity," Nature, 256:495-7 (1975).
Morath, et al., "Structure-function relationship of cytokine induction by lipoteichoic acid from *Staphylococcus aureus*," J. Exp. Med. 193(3), p. 393-397 (2001).
PCT Search Report for PCT/US05/003040, dated Mar. 8, 2006.
Marcaurelle, L., et al., "Synthesis of oxime-linked mucin mimics containing tumor-related Tn and sialyl Tn antigens," Organic Letters, vol. 3, No. 23, p. 3691-3694 (2001).
PCT Patentability Report for PCT/US05/003040, dated Jul. 29, 2006.
Renaudet & Dumy, "Chemoselectively template-assembled glycopeptides presenting clustered cancer related t-antigen," Tetrahedron Letters, vol. 45, No. 1, p. 65-68 (Jan. 2004).
"2-Cyanopyridazin-3(2H)-ones: effective and chemoselective electrophilic cyanating agents," Kim, et al., Tetrahedron, vol. 61, Jun. 2005, pp. 5889-5894.
Webb, R.R., et al., "Synthesis of 1-(aminooxy)-4-A(3-nitro-2-pyridyl) dithiou butane and 1-(aminooxy)-4-A(3-nitro-2-pyridyl) dithiou but-2-ene, novel heterobifunctional cross-linking reagents," Bioconjugate Chemistry, ACS, Washington, DC, US, vol. 1, No. 2, p. 96-99 (1990).
Brask, J. et al., "Carbopetptides: chemoselective ligation of peptide aldehydes to an aminooxy-functionalized D-galactose template," Journal of Peptide Science, vol. 6, p. 290-299 (2000).
Zeng, W. et al., "Assembly of synthetic peptide vaccines by chemoselective ligation of epitopes: influence of different chemical linkages and epitope orientations on biological activity," Vaccine, Butterworth Scientific, Guildford, GB, vol. 19, No. 28-29, p. 3843-3852 (Jul. 16, 2011).
Kubler-Kielb, J., et al., "A new method for conjugation of carbohydrates to proteins uing an aminooxy-thiol heterobifunctional linker," J. Org. Chem., vol. 701, p. 6987-6990 (Jul. 2005).
PCT Patentability Report for PCT/US2010/061133, dated Jun. 19, 2012.
Katritzky, et al., "C-Cynation with 1-Cyanobenzotriazole," ARKIVOC, 2007(iii), pp. 5-12.
PCT Search Report for PCT/US2010/055107, dated Jul. 28, 2011.
PCT Patentability Report for PCT/US2010/055107, dated Jul. 28, 2011.
R. Wong & H, Tse, Lateral Flow Immunoassay, Humana Press (2009).
Bioconjugate Protocols: Strategies and Methods (Methods in Moldecular Biology) Christof M. Niemeyer (Editor) Humana Press (2009).

\* cited by examiner

SIMPLE METHOD FOR SIMULTANEOUS REMOVAL OF MULTIPLE IMPURITIES FROM CULTURE SUPERNATANTS TO ULTRALOW LEVELS

REFERENCE TO RELATED APPLICATIONS

This application claims priority to U.S. Provisional Application No. 61/327,238 of the same title filed Apr. 23, 2010, the entirety of which is hereby incorporated by reference.

BACKGROUND

1. Field of the Invention

This invention is directed to a method for simultaneously removing, preferably in one step, multiple impurities from crude sample containing products produced by cell culture or fermentation and, in particular, the removal of contaminants such as media components, proteins, nucleic acids, lipids, and lipopolysaccharides to ultralow levels. The product may be produced by yeast, bacterial or mammalian cells with impurities reduced to ultralow level of 91% to 99.9% as compared to the purified target substance. The invention is also directed to the products that have been purified according to this method.

2. Description of the Background

Polysaccharides, proteins and nucleic acids are synthesized by various organisms such as yeast, bacteria, and mammalian cells, which can be produced by fermentation for commercial purpose in the applications of human, veterinary or diagnostic use. Industrial production of biotechnological product from these organisms is primarily done by fermentation in the applications of products for human, veterinary or diagnostic use. In addition to biosynthetic products produced during fermentation, media nutrients and components also contribute contaminants. It is generally necessary to produce extremely pure products with ultra-low levels of impurities like protein, lipid, nucleic acid and lipopolysaccharides from crude starting materials such as fermentation fluids. In addition to biosynthetic products produced during fermentation, media nutrients also contribute contaminants. Product purification typically involves multiple and complex steps to reduce impurity levels to acceptable levels. Conventional processes for removing impurities include extraction, chromatography, precipitation, ultra-filtration, and many others. Multiple and complex steps adversely affect yield, quality, stability, processing time and process operations. Further, these processes are expensive to run, require a high degree of skill to perform, and a significant amount of time to reduce impurity levels.

U.S. Pat. No. 5,747,663 relates to a process for reduction or removal of endotoxin from biotechnologically derived therapeutic compositions. The process has incorporated incubation with non-ionic detergent prior to chromatographic purification. The chromatographic medium claimed is anion exchange material. The chromatographic purification involves use of sodium chloride salt for washing.

U.S. Pat. No. 6,428,703 relates to a process for reduction or, removal of endotoxin from biological macromolecules. The process has incorporated treatment with non-ionic detergent without incubation period prior to the chromatographic purification. The chromatographic medium is anion exchange material. The other element is the anion exchanger retains the macromolecules and the purified macromolecule is eluted from the exchanger.

Conventional purification procedures are limited and do not result in products with ultra-low levels of impurities without extensive effort. Thus, there exists a need to develop a simple purification method to achieve high purity with ultralow levels of impurities of such biosynthetic products from culture supernatants, cell extracts, plant extracts or crude lysate.

SUMMARY OF THE INVENTION

The present invention overcomes the problems and disadvantages associated with current strategies and designs, and provides new tools and methods for simultaneous removal of multiple contaminants from culture supernatants, cell extracts, plant extracts or crude lysate. The method may also be applied to partially purified products to reduce the contaminants or undesired impurities to ultralow levels. Ultralow levels of impurities are levels that are preferably from 91% to 99.9% reduced as compared to unpurified substances. The invention may also be used in conjunction with additional purification steps to further enhance the purity of the target and reduce the level of contaminants.

One embodiment of the invention is directed to a purification process comprising: contacting a mixture containing a target substance and one or more contaminants to a chromatography matrix; washing the bound target substance with one or more buffers preferably at least one of which comprises a synergistic combination of a lyotropic agent or an organic solvent, a detergent, and a salt component; desorbing the bound target substance from the matrix, and collecting the target substance wherein the concentration of the one or more contaminants is preferably reduced by 91% to 99.9% as compared to the mixture. Preferably the target substance is one or more of an anionic polysaccharide, an anionic protein, a protein, a polysaccharide, an anionic molecule, a cationic molecule, or a nucleic acid, and the mixture contains one or more contaminants derived from yeast, bacteria, or cell culture fermentation, which may include media components, nucleic acids, proteins, lipids, and/or lipopolysaccharides.

Also preferably the chromatography matrix is or contains an anion exchange chromatography sorbent, a cation exchange chromatography sorbent, a hydrophobic interaction chromatography sorbent, mixed mode chromatography sorbent or a Cibacron-Blue pseudoaffinity chromatography sorbent or resins. Alternatively, the chromatography matrix may be a non sorbent chromatography such as a membrane or monolith chromatography devices. Accordingly, the chromatography matrix may involve anionic, cationic, hydrophobic or mixed mode sorbents as media or membrane. Washing may involve one, two, three or more buffers, wherein washing is performed sequentially or independently. Preferably the first buffer contains from 2 to 30% isopropanol, 10 to 2,000 mM of salt, and 0.01 to 1% TRITON® X-100 (a nonionic detergent) at a suitable pH. Preferably the second buffer contains 1 to 8 molar urea, 10 to 2000 mM of salt, and 0.01 to 1% TRITON® X-100 at a suitable pH. Preferably the third buffer contains a salt concentration different than the concentration of salt of the eluent depending in part on the chemical or physical characteristics of the target substance and also the chromatography matrix.

The bond target is desorbed preferably with an eluent containing a salt concentration that is different than the salt concentration of one or more of the wash buffers. Preferably the concentration of the one or more contaminants in the eluate is substantially reduced as compared to the concentration or amount of contaminants in the mixture before purification. More preferred, reduction is at least 91% and more preferably from 91% to 99.9% reduced.

Also preferably the chromatography matrix contains an anion exchange chromatography sorbent. Anionic species are acidic and have a negative charge. Contaminants, such as lipids, lipopolysaccharides, nucleic acids (e.g. are highly charged with repeating ionic groups, as are the anionic polysaccharides), are also anionic species as are many host cell proteins and media contaminants. The method of the invention purifies anionic target products despite this similarity in charge.

Another embodiment of the invention is directed to process for the purification of a target comprising: adsorbing a mixture containing the target and one or more contaminants to an ion exchange chromatography matrix, wherein at least one of the one or more contaminants comprises an endotoxin; washing the bound target with one or more wash buffers wherein at least one wash buffer contains a synergistic combination of a lyotropic agent or an organic solvent, a detergent and a salt component; desorbing the bound target from the chromatography matrix; and collecting the desorbed target wherein the level of endotoxin is less than or equal to 3 UE/mg of target and preferably less than or equal to 2.5 UE/mg of target. Preferably the amount of the one or more contaminants is in the desorbed target is reduced by 91% to 99.9%, and washing involves only a single wash buffer.

Another embodiment of the invention is directed to a purified target substance obtained from the methods of the invention. Preferred targets include, for example, a meningococcal C polysaccharide, *Haemophilus influenzae* type b (Hib) polysaccharide, recombinant erythropoietin protein, or recombinant CRM197.

Other embodiments and advantages of the invention are set forth in part in the description, which follows, and in part, may be obvious from this description, or may be learned from the practice of the invention.

DESCRIPTION OF THE INVENTION

The present invention relates to the field of purification of biological products, particularly purification of substances from crude culture samples such that extremely low levels of contaminating materials remain. The purified substance may be, for example, proteins, polysaccharides, virus or nucleic acids that are used in the preparations of medicines for the treatment of diseases, vaccines, therapeutic drugs and diagnostic kits and components, which may be useful for humans or other animals.

The invention is directed to product purification processes that are performed preferably in one-step for the simultaneous removal of multiple impurities and particularly, to purification from bacterial, yeast, plant and other cell cultures and fluids such that the final products obtained contain extremely low levels of contaminating substances. These contaminants include but are not limited to one or more of proteins, lipids, nucleic acids, endotoxin, cell debris, and lipopolysaccharides. The invention comprises processes for purification of a desired product from a mixture such as, for example, a cell lysate, a cell extract, a cell culture or other crude sample which may be bacterial (prokaryotic) or cellular (eukaryotic) in origin. The target molecule or substance is preferably a protein, polysaccharide or nucleic acid that preferentially adsorbs or binds to the chromatography matrix. The chromatography matrix may be a single form of chromatography material or a combination of materials, for example, arranged in a step-like configuration. Binding may be through ionic, hydrophobic or hydrophilic interaction. Preferred chromatography matricies include. but are not limited to an ion exchange matrix such as a SEPHAROSE® (a chromatographic medium), Cibacron Blue affinity media, or a mixed mode chromatography matrix. The one or more washes preferentially involve simultaneous use of urea/detergent/salt and/or solvent/detergent/salt in the various washes on the column prior to the elution of desired product. The preferred method of the invention involves an ion exchange matrix such as Q-Sepharose, a washing agent such as urea or isopropanol, detergent such as TRITON® X100, and salt such as sodium chloride in the one or more chromatographic wash buffers. The eluate is then collected and contains highly purified target substance with an ultra-low level of impurities. This method can be applied to polysaccharides, proteins or nucleic acids of interest derived from recombinant or wild yeast, bacteria or mammalian cell lines and extracellular, periplasmic or intracellular product. The synergistic effect of concomitant use of these components in wash buffers allows for the removal of multiple contaminants during the washing step on chromatographic sorbents and leads to highly pure product in the eluate.

The invention is directed to a purification process preferably comprising the steps of: (1) binding of a mixture containing the target substance and one or more contaminants to a chromatography matrix; (2) washing the bound target substance with one or more buffers containing a combination of a lyotropic agent or organic solvent, a detergent, and a salt component; (3) desorbing the target substance from the chromatography matrix which may be with an elution buffer (the eluent); and (4) collecting the target in the eluate wherein the eluate preferentially contains target with ultra low levels of contaminants. Binding involves preferential adsorption of the target to the matrix through ionic, hydrophobic, hydrophilic or covalent interaction. Preferably the washes are given sequentially or any single wash may be performed independently. Further, one or more of these washes may be followed by another wash of salt buffer with salt concentration different than elution buffer before the elution of product of interest, depending on the product of interest. Target is collected in the eluate upon contacting a deadsorbing eluent to the target-bound chromatography matrix. The resulting eluate contains increased concentrations of target and ultra-low concentrations of contaminants. Ultra low levels of contaminants are substantial reductions of impurities that were present in the starting material (e.g. the target substance with impurities). Substantial reductions are preferably reductions of 85% or greater, more preferably 90% or greater, more preferably 95% or greater, and still more preferably in the range of 91% to 99.9%, and even more preferably to the degree that impurities are undetectable by convention and industry standard detection methods and devices.

A significant feature of the purification method is the synergistic effect on simultaneous removal of multiple contaminants with the concomitant use of solvent, urea, detergent and salt during the washing step on chromatographic sorbent. Typical contaminants include media and other components that were introduced to a culture to stimulate growth as well as nucleic acids, proteins, lipids, nucleic acids, and lipopolysaccharides, and any other unwanted or undesirable substance that may be present in the material to be purified.

The method of the invention involves simultaneous reduction of anionic lipopolysaccharide like endotoxin as well as protein, and nucleic acid contaminants from culture supernatant to ultra low levels. An incubation step is not always necessary prior to chromatographic purification, and preferably not required. Endotoxin levels can be reduced to ultra low level such as, preferably, 3 UE/mg or less as compared to conventional processes which are only able to achieve low levels of endotoxin with considerable effort. Preferably endotoxin levels are reduced to 2.5 UE/mg or less, and even more preferably to 2.0 UE/mg less. The method of the invention is also less time consuming, cost effective, reproducible as compared to conventional approaches.

The invention is preferably directed to a process for purification of a desired product by ion exchange chromatography with simultaneous treatment with urea/detergent/salt and/or solvent/detergent/salt in the various washes on the column prior to the elution of the desired product. Conventional chromatography sorbents may be used for purification as well as well as membrane and monolith devices. Preferred anion ion exchange matrices include, but are not limited to Q Sepharose, DEAE Fast Flow (GE Healthcare), and Q HyperCel (Pall Life Sciences), all of which are commercially available. Examples of preferred cation exchange matrices include, but are not limited to S SEPHAROSE®, CM SEPHAROSE®, S Source (GE Healthcare, CM Ceramic and S HyperCel (Pall Life Sciences). Examples of mixed mode sorbents include, but are not limited to MEP, HEA PPA HyperCel (Pall Life Sciences), Ceramic hydroxyapatite (Bio-Rad) and MMC (GE Healthcare). Examples of Cibacron blue dye-ligand pseudoaffinity chromatography sorbent include Blue-Sepharose (GE Healthcare). Examples of suitable membranes include, but are limited to Q and S SARTOBIND® (a hydrophobic interaction membrane) and Mustang devices (Sartorius and Pall Life Sciences, respectively), and Phenyl Sartobind hydrophobic interaction membrane (Sartorius). A variety of suitable monolith chromatography devices are also available (WA Separations, Wilmington, Del.).

Examples of preferred lyotropic agents include urea, guanidine hydrochloride, arginine and sodium thiocyanide. Examples of preferred detergents include TRITON® X-100, Polysorbate 20, Polysorbate 80, sodium dodecyl sulfate (SDS), and sodium sarcosine. Examples of preferred organic additives include ethanol, isopropanol (IPA), glycerol ethylene glycol, and propylene glycol. Examples of preferred salts include sodium chloride, potassium chloride, ammonium sulfate and sodium phosphate. Again, all of the aforesaid agents, detergents, additives, and salts are well-known and commercially available.

Products that are purified according to the method of the invention include ones which may be obtained from a large variety of biological fluids including yeast, bacteria, plant, and cell culture fermentation and, preferably, bacterial cell supernatants. Preferably, products purified are involved in the manufacture of therapeutic proteins, vaccines and may include anionic polysaccharides, anionic protein, and nucleic acids. Additional products that can be purified by the methods of the invention include, but are not limited to, culture supernatants of eukaryotic cells and biological samples of serum and other bodily fluids that are utilized in medical procedures.

Preferred bacterial products that can be purified using the methods of the invention include, for example, *Neisseria meningiditis* serotype B alpha 2-8 linked polysaccharide, *Neisseria meningiditis* serotype C capsular polysaccharide, *Salmonella* Vi polysaccharide, delipidataed lipopolysaccahrides and lipooligosaccharides, and *Haemophilus influenzae* type B-PRP capsular polysaccharide. These examples are polysaccharides used for vaccine preparations and, therefore, preferably have ultra low levels of impurities to meet or exceed guidelines established by the U.S. Food and Drug Administration and similar authorities around the world. Preferred protein products that can be purified using the methods of the invention include, for example, recombinant erythropoietin from cell culture fermentation and recombinant cross reacting material 197 from bacterial fermentation.

According to the method of the invention, the product may be purified from cells containing product or from the culture supernatant, or both. The cells and culture supernatant are preferably separated by either centrifugation or cross flow filtration. For extracellular product, the culture supernatant is preferably directly processed through the method of invention, whereas for intracellular or periplasmic space product, products are preferably recovered from both culture supernatant and/or cells. The protein is extracted from the cells by chemical means like osmotic shock in sucrose or physical means like homogenization. Culture supernatant and/or extract or lysate containing product is then preferably processed through chromatographic purification step.

Most of the polysaccharides from bacterial fermentation and mammalian cell recombinant proteins are derived from supernatant whereas other recombinant proteins and nucleic acid are derived from cells of yeast and bacteria.

Chromatography Step

This purification step comprises ion exchange, hydrophobic interaction, Cibacron Blue pseudo-affinity or mixed mode chromatography sorbent in a column mode or batch mode. For example, for anion exchange Q-SEPHAROSE® may be used, and phenyl SEPHAROSE® sorbent for hydrophobic interaction. Either of the following mentioned washes or in combination can be given, order of wash sequence can also be altered appropriately.

Column Preparation

A column is packed according to the manufacturer instructions. The column is sanitized and equilibrated with equilibration buffer until stable baselines for RI, absorbance$_{nm}$ and conductivity are obtained. For ion exchange low molarity suitable Equilibration Buffer is used with desired pH like 20 mM Tris buffer (pH 8) and phosphate buffer (pH 7) whereas for hydrophobic interaction the buffer has a high salt content e.g., 2.5 M NaCl.

Column Loading (Crude Sample)

Culture supernatant is adjusted to desired conductivity and by addition of acid/alkali/buffer/water/salt. The column is then loaded with culture supernatant or lysate or extract containing sample at a recommended flow rate. After loading, the column is washed again with equilibration buffer to remove any residual material not tightly bound to the sorbent.

Column Wash I (Solvent)

The column is washed with suitable column volumes of Wash Buffer-I containing appropriate concentrations of solvent like isopropanol, detergent such as preferably TRITON® X-100 and salt such as preferably NaCl in an Equilibration Buffer at a suitable flow rate until stable baselines for Refractive index, Absorbance and conductivity are obtained to monitor protein, nucleic acid, lipid and lipopolysaccharide impurities.

Column Wash II (Lyotropic agent)

The column is washed with suitable column volumes of Wash Buffer-II containing appropriate concentrations of chaotropic agent like urea, detergent like TRITON® X-100 and salt like NaCl in an equilibration buffer at a suitable flow rate until stable baselines for Refractive index, Absorbance and conductivity are obtained to remove any protein, nucleic acid, lipid and lipopolysaccharide impurities.

Column Wash III (Salt)

The column is washed with suitable column volumes of Wash Buffer III containing appropriate concentration of salt like NaCl different to that of elution concentration in an equilibration buffer at a suitable flow rate until stable baselines for Refractive Index, absorbance and conductivity are obtained to monitor removal of protein, nucleic acid and lipopolysaccharide impurities.

Elution Step (Product)

Desired product is eluted from the column with Elution Buffer containing appropriate concentration of salt or any other elution agent at a suitable flow rate. Elution may be monitored using refractive index or Absorbance detection. Appropriate column volumes of Elution Buffer is collected which contains the desired product. Column can be regenerated by passing appropriate buffer with salt and sanitizing agent like sodium hydroxide. It thus removes multiple impurities, different in nature, in a simple method of purification, preferably in a single step, on a chromatography sorbent.

The following examples illustrate embodiments of the invention, but should not be viewed as limiting the scope of the invention.

EXAMPLES

As indicated herein, the invention is illustrated for the single method of simultaneous removal of multiple impurities from crude samples of culture supernatant to ultralow level by chromatographic techniques. In one method of the invention, the adsorption sorbents are anion exchangers with specific elution conditions such that the resultant purified product exhibits a very low content of contaminating protein, lipid, nucleic acid and lipopolysaccharide.

Example 1

Meningococcal C Polysaccharide

Capsular polysaccharide was derived from bacterial fermentation. The culture supernatant containing products was obtained by centrifugation or cross flow filtration of fermentation broth.

Anion Exchange Chromatography Sorbent: Q-Sepharose
Buffers:
  Equilibration Buffer (20 mM Phosphate buffer pH 7.5)
  Wash Buffer-I (15% IPA+0.25% TRITON® X-100+0.3 M NaCl, pH 7.5)
  Wash buffer-II (6 M Urea+0.25% TRITON® X-100+0.3 M NaCl, pH 7.5)
  Wash Buffer III (20 mM phosphate buffer+0.3 M NaCl, pH 7.5)
  Elution buffer (20 mM Phosphate buffer, 0.5 M NaCl, pH 7.5)
  Regeneration Buffer (1 M NaCl and 0.5 M NaOH)

A column with 20 cm inner diameter (Pharmacia, BPG 200/500) was packed according to the manufacturer instructions using 6 L Pharmacia Q Sepharose Fast flow sorbent with a fixed bed height of ~200 mm. The column was washed with 10 column volumes (CV) of water for Injection (WFI) and then charged and sanitized using 5 CV of 1 M sodium chloride solution with 0.5 M NaOH solution using the flow rates recommended by the manufacturer.

Column Loading

Culture supernatant was adjusted to pH 7.5 by acid/alkali addition and conductivity to $\leq$10 mS/cm by water for injection dilution. The column was neutralized with Equilibration Buffer (20 mM Phosphate buffer pH 7.5), for ~15 CV until stable baselines for $A_{280nm}$ and conductivity were obtained. The column was then loaded with culture supernatant containing sample at a flow rate of 60 cm/h. After loading, the column was washed again with 3 CV of equilibration buffer (20 mM Phosphate buffer pH 7.5) to remove any residual material not tightly bound to the sorbent.

Column Wash I

The column was washed with 3 CV of Wash Buffer-1 (15% IPA+0.25% TRITON® X-100+0.3 M NaCl, pH 7.5) at a flow rate of 60 cm/h until stable baselines for Refractive index, $A_{280nm}$ and conductivity was obtained to remove any protein, nucleic acid, lipid and lipopolysaccharide impurities.

Column Wash II

The column was washed with 3 CV of Wash buffer-II (6 M Urea+0.25% TRITON® X-100+0.3 M NaCl, pH 7.5) at a flow rate of 60 cm/h until stable baselines for Refractive index, $A_{280nm}$ and conductivity were obtained to further remove any protein, nucleic acid, lipid and lipopolysaccharide impurities.

Column Wash III

The column was washed with 3 CV of Wash Buffer III (20 mM phosphate buffer+0.3 M NaCl, pH 7.5) at a flow rate of 60 cm/h until stable baselines for Refractive index, $A_{280nm}$ and conductivity were obtained to further remove any protein, nucleic acid and lipopolysaccharide impurities.

Elution Step

Men C polysaccharide product was eluted from the column with Elution Buffer (20 mM Phosphate buffer, 0.5 M NaCl, pH 7.5) at a flow rate of ~60 cm/h in the form of a single Refractive index/$A_{224}$ peak. Continue elution until Refractive index/$A_{224nm}$ absorbance began to decrease below 5% of the peak value. About 2 column volumes of Elution Buffer were used in this elution step. The column was regenerated by passing 1 M NaCl with 0.5 N NaOH.

Protein, DNA, lipid, lipopolysaccharide, host cell protein, host cell DNA and target polysaccharide analysis was performed on samples of the load, and eluate taken during the chromatographic run. Polysaccharide and protein were assayed using standard methods, polysaccharide using phenol sulfuric acid method, nucleic acid by absorbance at 260 nm, lipid by orcinol method and protein using Lowry method. Host cell DNA was analyzed by RT-PCR whereas host cell protein assayed by ELISA. Lipopolysaccharide was determined using a kinetic turbidimetric assay for endotoxin. From Lipopolysaccharide standards, value for unknown sample was derived in units of EU/ml. Results are shown in Table 1.

TABLE 1

| Product | Protein | Nucleic acid | Lipopolysaccharide | Lipid | Host cell protein | Host cell DNA |
| --- | --- | --- | --- | --- | --- | --- |
| Load (Culture supernatant) | 15% | 1% | 100,000 EU/mg polysaccharide | | | |
| Eluent (Purified product) | <0.05% | <0.05% | <5 EU/mg polysaccharide | <0.3% | <5 ng/mg | <5 pg/mg |

As can be determined in Table 1, the Q-Sepharose column reduced the Lipopolysaccharide level from initial 100,000 EU/mg polysaccharide to less than or equal to 5 EU/mg LPS in the eluate. The target polysaccharide was hound to the sorbent and recovery was 70% based on assay results. Polysaccharide eluted off of the column in 20 mM phosphate buffer, 0.5 M NaCl, pH 7.5. Analysis showed that most of the nucleic acid and lipopolysaccharide was bound to the sorbent, but came off during the washing steps. The majority of small media proteins and lipids did not bind to the matrix and were found in the flow through. Significantly, the polysaccharide purity was more than 99% in the final product.

Example 2

Haemophilus influenzae Type b (Nib) Polysaccharide

The culture supernatant containing product was obtained by centrifugation or cross flow filtration of fermentation broth to separate the bacterial cells. Supernatant obtained containing polysaccharide with impurities was processed through one step method of purification.

Anion exchange chromatography: Sorbent: Q-Sepharose
Buffers:
  Equilibration Buffer (20 mM Phosphate buffer pH 7.5)
  Wash Buffer-I (15% IPA+0.25% TRITON® X-100+0.3 M NaCl, pH 7.5)
  Wash buffer-II (6 M Urea+0.25% TRITON® X-100+0.3 M NaCl, pH 7.5)
  Wash Buffer III (20 mM phosphate buffer+0.3 M NaCl, pH 7.5)
  Elution buffer (20 mM Phosphate buffer, 0.5 M NaCl, pH 7.5)
  Regeneration Buffer (1 M NaCl and 0.5 M NaOH)

A column with 20 cm inner diameter (Pharmacia, BPG 200/500) was packed according to the manufacturer instructions using 6 L Pharmacia Q Sepharose Fast flow sorbent with a fixed bed height of ~200 mm. The column was washed with 10 column volumes (CV) of water for Injection (WFI) and then charged and sanitized using 5 CV of 1 M sodium chloride solution with 0.5 M NaOH solution using the flow rates recommended by the manufacturer.

Column Loading

Column was neutralized with Equilibration Buffer (20 mM Phosphate buffer pH 7.5), for 15 CV until stable baselines for Refractive index, $A_{280nm}$ and conductivity are obtained. Culture supernatant was adjusted to pH 7.5 by acid/alkali addition and conductivity to less than or equal to 10 mS/cm by water for injection dilution. The column was then loaded with culture supernatant containing sample at a flow rate of 60 cm/h. After loading, the column was washed again with 3 CV of equilibration buffer (20 mM Phosphate buffer pH 7.5) to remove any residual material not tightly bound to the sorbent.

Column Wash I

The column was washed with 3 CV of Wash Buffer-I (15% IPA+0.25% TRITON® X-100+0.3 M NaCl, pH 7.5) at a flow rate of 60 cm/h until stable baselines for Refractive index, $A_{280nm}$ and conductivity was obtained to remove any protein, nucleic acid, lipid and lipopolysaccharide impurities.

Column Wash II

The column was washed with 3 CV of Wash buffer-II (6 M Urea+0.25% TRITON® X-100+0.3 M NaCl, pH 7.5) at a flow rate of 60 cm/h until stable baselines for Refractive index, $A_{280nm}$ and conductivity were used to monitor protein, nucleic acid, lipid and lipopolysaccharide impurities.

Column Wash III

The column was washed with 3 CV of Wash Buffer III (20 mM phosphate buffer+0.3 M NaCl, pH 7.5) at a flow rate of 60 cm/h until stable baselines for Refractive index, $A_{280nm}$ and conductivity was obtained to further remove any protein, nucleic acid, lipid and lipopolysaccharide impurities.

Elution Step

Polysaccharide was eluted from the column with elution buffer (i.e. eluent) (20 mM phosphate buffer, 0.5 M NaCl, pH 7.5) at a flow rate of ~60 cm/h in the form of a single Refractive index/$A_{224}$ peak. Continue elution until Refractive index/$A_{224nm}$ absorbance began to decrease below 5% of the peak value. About 2 column volumes of eluent are necessary in this elution step. The column was regenerated with 1 M NaCl with 0.5 N NaOH.

The process reduced the lipopolysaccharide level to less than 3 EU/mg polysaccharide. The polysaccharide recovery was 60% based on assay results, which was bound to the sorbent. Polysaccharide eluted off of the column in 20 mM phosphate buffer, 0.5 M NaCl, pH 7.5. Analysis showed that most of the nucleic acid and lipopolysaccharide were bound to the sorbent, but came off during washing steps. The results achieved are shown in Table 2.

TABLE 2

| Product | Protein | Nucleic acid | Lipopoly-sachharide | Host cell protein | Host cell DNA |
|---|---|---|---|---|---|
| Load (Culture supernatant) | 20% | 2% | 120,000 EU/mg polysaccharide | | |
| Eluate (Purified product) | <0.5% | <0.1% | <3 EU/mg polysaccharide | <50 ng/mg | <20 pg/mg |

Protein, DNA, lipid, lipopolysaccharide, host cell protein, host cell DNA and desired polysaccharide analysis was performed on samples of the load, and eluate taken during chromatographic run. The target polysaccharide and residual protein were assayed with standard methods, polysaccharide using phenol sulfuric acid method, nucleic acid by absorbance at 260 nm, lipid by the orcinol method and protein using Lowry method. Host cell DNA analyzed by RT-PCR and host cell protein by ELISA. Lipopolysaccharide was assayed by kinetic turbidimetric assay for endotoxin. Using lipopolysaccharide standards, the value for unknown sample was derived in units of EU/ml.

The majority of small media proteins and lipids were in the flow through. This elution fraction was processed further by diafiltration for the removal of salt as desired. The polysaccharide purity obtained was more than 99%.

Example 3

Recombinant Erythropoietin Protein

The culture supernatant containing product was obtained by cross flow filtration of fermentation broth to separate the cells. Supernatant obtained containing protein with media components and impurities was processed through one step method of purification. The culture used was recombinant mammalian cell CHO cell line for erythropoietin production.

Hydrophobic interaction chromatography: Sorbent: TOYO-PEARL® (Toyopearl-butyl; Tosohas)
Buffers:
  Equilibration Buffer (20 mM Phosphate buffer pH 7.2, 0.75 M NaCl)
  Wash buffer (19% IPA+0.75 M NaCl, pH 7.2)
  Elution buffer (27% IPA+0.75 M NaCl, pH 7.2)
  Regeneration Buffer (1 M NaOH)

A column with 20 cm inner diameter (GE, BPG 200/500) was packed according to the manufacturer instructions using 6 L GE Butyl Sepharose sorbent with a fixed bed height of ~200 mm. The column was washed with 10 column volumes (CV) of water for Injection (WFI) and then sanitized using 5 CV of 0.5 M NaOH solution using the flow rates recommended by the manufacturer.

Column Loading

Column was neutralized with Equilibration Buffer (27% IPA, 20 mM phosphate buffer pH 7.2 and 0.75 M NaCl), for 15 CV until stable baselines for Refractive index, $A_{280nm}$ and conductivity were obtained. The column was then loaded with culture supernatant containing sample at a flow rate of 60 cm/h. Culture supernatant was adjusted to pH 7.2 by acid/alkali addition and conductivity to greater than or equal to 200 mS/cm by sodium chloride addition. After loading, the column was washed again with 3 CV of equilibration buffer to remove any residual material not tightly bound to the sorbent.

Column Wash

The column was washed with 3 CV of Wash Buffer-I (17% IPA+0.75 M NaCl, pH 7.2) at a flow rate of 60 cm/h until stable baselines for $A_{280nm}$ and conductivity were obtained to remove any protein, nucleic acid, lipid and lipopolysaccharide impurities.

Elution Step

Protein was eluted from the column with Elution Buffer (20 mM Phosphate buffer, pH 7.5) at a flow rate of ~60 cm/h in the form of a single $A_{224}$ peak. Elution was continued until $A_{224nm}$ absorbance begins to decrease below 5% of the peak value. About 2 column volumes of Elution Buffer are necessary in this elution step. The column was regenerated by passing 1 N NaOH through as a Regeneration Buffer.

As shown in Table 3, lipopolysaccharide level was reduced from 120,000 EU/mg polysaccharide to less than or equal to 2.3 EU/mg polysaccharide. The protein recovery was 80% which is bound to the sorbent. Protein eluted off the column in 20 mM Phosphate buffer, pH 7.5. Analysis showed that most of the nucleic acid and polysaccharide were not bound to the sorbent, and bound lipopolysaccharides come off during washing steps.

TABLE 3

| Product | Protein Contamination | Lipopoly-saccharide | Host cell protein | Host cell DNA |
| --- | --- | --- | --- | --- |
| Eluate (Purified product) | <1% | <2.3 EU/mg | <100 pg/mg | <10 pg/mg |

The majority of small media proteins and lipids came off during the washes. The protein purity obtained was more than 99%.

Example 4

Recombinant CRM197

Recombinant protein CRM197, cross reacting material, a mutant of diphtheria toxin, was derived from bacterial fermentation. As the protein was located in periplasmic space, product was recovered from both culture supernatant and cells. The cells and culture supernatant were separated by either centrifugation or cross flow filtration. The protein was extracted from the cells by chemical means like osmotic shock in sucrose or physical means like homogenization. Supernatant and/or extract containing product was then processed through chromatographic purification step as follows.

1. Anion Exchange Chromatography: Sorbent: CaptoQ

Buffers:
   Equilibration Buffer (15 mM Tris buffer pH 8)
   Wash Buffer-I (5% IPA+0.05% Triton X-100+0.05 M NaCl, 15 mM Tris pH 8)
   Wash Buffer-II (15 mM Tris buffer+0.08 M NaCl, pH 8)
   Elution buffer (15 mM Tris+0.2 M NaCl, pH 8)
   Regeneration Buffer (1.5 M NaCl and 1 M NaOH)

Cells obtained from 20 L fermentor were subjected to extraction by osmotic shock using 30% Sucrose, 15 mM Tris pH 7.4, 5 mM EDTA and 50 mM Tris pH 7.4. The filtered extract (45 L) was loaded on Capto-Q sorbent in 10 mM Tris buffer pH 8.0 and eluted using 0.2 M NaCl in 10 mM Tris buffer pH 8. A column with 30 cm inner diameter (GE, BAG 300/500) was packed according to the manufacturer instructions using 10 L Capto Q (GE) sorbent. The column was washed with 3 column volumes (CV) of water for Injection (WFI) and then charged using 0.5 CV of 1 M Tris pH•8 with flow rates as recommended by the manufacturer.

Column Loading

The column was equilibrated with Equilibration Buffer (15 mM Tris buffer pH 8), for about 1 CV until stable baselines for $A_{280nm}$ and conductivity were obtained. The column was then loaded with filtered extract containing sample at a flow rate of 212 L/h (240 cm/h). After loading, the column was washed again with about 1 CV of equilibration buffer (15 mM Tris buffer pH 8) to remove any residual material not tightly bound to the sorbent.

Column Wash I

The column was washed with 2 CV of Wash Buffer-I (5% IPA+0.05% Triton X-100+0.15 M NaCl, pH 7.5) at a flow rate of 240 cm/h until stable baselines for $A_{280nm}$ and conductivity were obtained to remove any protein, nucleic acid, lipid and lipopolysaccharide impurities. The column was washed again with ~2 CV of equilibration buffer (15 mM Tris buffer pH 8).

Column Wash II:

The column was Washed with 2 CV of Wash buffer-II (15 mM Tris buffer+0.08 M NaCl, pH 8) at a flow rate of 240 cm/h until stable baselines for $A_{280nm}$ and conductivity are obtained to further remove any protein and nucleic acid impurities.

Elution Step

Protein product was eluted from the column with Elution Buffer (15 mM Tris+0.2 M NaCl, pH 8) at a flow rate of 240 cm/h in the form of a single $A_{280}$ peak. Continue elution until $A_{280nm}$ absorbance begins to decrease below 5% of the peak value. About 2 column volumes of Elution Buffer were necessary in this elution step. Column was regenerated by passing 2 column volumes of 1.5 M NaCl with 1 N NaOH.

2. Hydrophobic Interaction Chromatography: Sorbent: Phenyl Sepharose

Buffers:
   Equilibration Buffer (10 mM phosphate buffer pH 7.4+1.5 M NaCl)
   Wash Buffer-I (1 M NaCl+10 mM phosphate buffer pH 7.4)
   Wash Buffer-II (0.3 M NaCl+10 mM phosphate buffer pH 7.4)
   Elution buffer (10 mM phosphate buffer pH 7.4)
   Regeneration Buffer (20% IPA)

The Capto-Q IEC eluate was loaded on Phenyl Sepharose sorbent in 10 mM phosphate buffer pH 7.4 and eluted using 10 mM phosphate buffer pH 7.4. A column with 30 cm inner diameter (GE, BPG 300/500) was packed according to the manufacturer instructions using 10 L Phenyl Sepharose (GE) sorbent.

Column Loading

Column was equilibrated with Equilibration Buffer (10 mM phosphate buffer pH 7.4+1.5 M NaCl), for ~1 CV until stable baselines for $A_{280nm}$ and conductivity were obtained. The column was then loaded with IEC eluate containing sample at a flow rate of 150 cm/h. After loading, the column was washed again with ~1 CV of Equilibration Buffer (15 mM Tris buffer pH 8) to remove any residual material not tightly bound to the sorbent.

Column Wash I

The column was washed with 2 CV of Wash Buffer-I (51 M NaCl+10 mM phosphate buffer pH 7.4) at a flow rate of 150 cm/h until stable baselines for $A_{280nm}$ and conductivity were obtained to remove any protein, lipid and lipopolysaccharide impurities. The column was washed again with about 2 CV of Equilibration Buffer.

Column Wash II

The column was washed with 2 CV of Wash buffer-II (0.3 M NaCl+10 mM phosphate buffer pH 7.4) at a flow rate of 150 cm/h until stable baselines for $A_{280nm}$ and conductivity were obtained to further remove any protein and lipid impurities.

Elution Step

Protein product was eluted from the column with Elution Buffer (10 mM phosphate buffer pH 7.4) at a flow rate of 150 cm/h in the form of a single $A_{280}$ peak. Continue elution until $A_{280nm}$ absorbance begins to decrease below 5% of the peak value. About 2 column volumes of Elution Buffer were necessary in this elution step. Column was regenerated by passing 2 column volumes of 20% IPA.

The method of purification involving Capto-Q and Phenyl Sepharose column reduced the lipopolysaccharide level to less than or equal to 100 EU/mg protein. Analysis showed that nucleic acid, protein impurities, lipids and polysaccharides come out in the various washes on Capto-Q sorbent. Resultant purified protein was highly pure due to combination of two chromatography steps involving washing steps of method of invention. A single step of chromatography (Capto-Q) alone with washing steps of method of invention leads to more than 85% purity. The target protein purity obtained was more than 99.9% with host cell protein less than 100 ng per mg protein and host cell DNA less than 50 ng per mg protein.

Example 5

Recombinant CRM197 with Cibacron-Blue

Recombinant protein CRM197, cross reacting material, a mutant of diphtheria toxin, was derived from bacterial fermentation. Being periplasmic, product was recovered from cell extract. The cells were separated by either centrifugation. The protein was extracted from the cells by chemical means like osmotic shock in sucrose. Extract containing product was then processed through chromatographic purification step as follows.

Cibacron Blue pseudoaffinity Chromatography: Sorbent: Blue-sepharose

Buffers:

Equilibration Buffer (15 mM Tris buffer pH 8)
    Wash Buffer-I (5% IPA+0.05% TRITON® 100+0.05 M NaCl, 15 mM Tris pH 8)
    Wash Buffer-II (15 mM Tris buffer+0.2 M NaCl, pH 8)
    Elution buffer (15 mM Tris+0.5 M NaCl, pH 8)
    Regeneration Buffer (8 M Urea)
    Cells obtained from 20 L fermentor were subjected to extraction by osmotic shock using 30% Sucrose, 15 mM Tris pH 7.4, 5 mM EDTA and 50 mM Tris pH 7.4. The filtered extract (45 L) was loaded on Blue sepharose sorbent in 10 mM Tris buffer pH 8.0 and eluted using 0.5 M NaCl in 10 mM Tris buffer pH 8. A column with 45 cm inner diameter (GE, BPG 450/500) was packed according to the manufacturer instructions using 20 L Blue Sepharose (GE) sorbent.

Column Loading

The column was equilibrated with Equilibration Buffer (15 mM Tris buffer pH 8), for about 1 CV until stable baselines for $A_{280nm}$ and conductivity were obtained. The column was then loaded with filtered extract containing sample at a flow rate of 240 L/h i.e. 150 cm/h. After loading, the column was washed again with about 1 CV of equilibration buffer (15 mM Tris buffer pH 8) to remove any residual material not tightly bound to the sorbent.

Column Wash I

The column was washed with 2 CV of Wash Buffer-I (5% IPA+0.05% TRITON® X-100+0.05 M NaCl, pH 8.0) at a flow rate of 150 cm/h until stable baselines for $A_{280nm}$ and conductivity were obtained to remove any protein, nucleic acid, lipid and lipopolysaccharide impurities. The column was washed again with about 2 CV of equilibration buffer (15 mM Tris buffer pH 8).

Column Wash II:

The column was washed with 2 CV of Wash buffer-II (15 mM Tris buffer+0.2 M NaCl, pH 8) at a flow rate of 150 cm/h until stable baselines for $A_{280nm}$ and conductivity are obtained to further remove any protein and nucleic acid impurities.

Elution Step

Protein product was eluted from the column with Elution Buffer (15 mM Tris+0.5 M NaCl, pH 8) at a flow rate of 150 cm/h in the form of a single $A_{280}$ peak. Continue elution until $A_{280nm}$ absorbance begins to decrease below 5% of the peak value. About 2 column volumes of Elution Buffer were necessary in this elution step. Column was regenerated by passing 2 column volumes of 8 M Urea.

The method of purification involving Blue Sepharose column reduced the lipopolysaccharide level to less than or equal to 500 EU/mg protein. Analysis showed that nucleic acid, protein impurities, lipids and polysaccharides come out in the flow through and various washes on Blue Sepharose sorbent. Resultant purified protein was highly pure with a chromatography step involving washing steps of method of invention. A single step of chromatography alone with washing steps of method of invention leads to more than 92% purity with nucleic acid less than 0.1%.

Example 6

Polysaccharide Purification with a Mixed Mode Sorbent

Neisseria meningiditis serotype B alpha 2-8 linked polysaccharide on a mixed mode sorbent.

| | |
|---|---|
| Equilibration buffer | 10 mM sodium phosphate, 25 mM NaCl, pH 7.5 |
| Wash Buffer-I | 15% IPA + 0.25% TRITON ® X-100 + 0.1M NaCl, pH 7.5 |
| Wash buffer-II | 6M Urea + 0.25% TRITON ® X-100 + 0.1M NaCl, pH 7.5 |
| Elution buffer | 25 mM sodium acetate + 0.5M NaCl, pH 5.0 |

A column packed with PPA HyperCel (Pall Life Sciences) is prepared according to the manufacturer's instructions and equilibrated with equilibration buffer. A partially purified extract of Neisseria meningiditis serotype B alpha 2-8 linked polysaccharide in buffer I is loaded onto the column at 60 cm/hr. The column is washed with Equilibration buffer and sequentially with Wash Buffers I and II, at 60 cm/hr. Each wash is continued until a stable absorbance and refractive index baseline is achieved. The colominic acid is eluted with Elution buffer.

Standard assays are performed to determine the concentration of colominic acid, host cell protein, nucleic acid, lipid and nucleic acid. The product is substantially free of contaminants.

Example 7

Purification of a Basic Protein on a Cation Ion Exchanger

Equilibration buffer: 50 mM sodium phosphate+50 mM NaCl, pH 6.0
Wash buffer I 50 mM Na phosphate+0.15% Na sarcosine+100 mM NaCl, pH 6.0
Wash buffer II 50 mM Na phosphate+0.15% Na sarcosine+150 mM Arginine, pH 6.0
Elution buffer 50 mM sodium phosphate+500 mM NaCl, pH 6.0

A column is packed with CM Ceramic (Pall Life Sciences) according to the manufacturer's instructions and equilibrated with equilibration buffer. Recombinant lysostaphin from an *E. coli* supernatant is clarified, diluted into equilibration buffer and filtered. The recombinant lysostaphin is loaded onto the column at 200 cm/hr and further washed with equilibration buffer. The column is then washed sequentially with the two wash buffers until the absorbance and refractive index returned to baseline. The product is then eluted with the elution buffer.

Standard assays are performed to determine the concentration of protein, host cell protein, nucleic acid, lipid and nucleic acid. Purity of the product is evaluated by SDS PAGE and reverse phase HPLC. The specific activity of lysostaphin is determined by a *staphylococcus* killing assay. The product is substantially free of contaminants.

Example 8

Purification of Using a Q Sartobind Ion Exchange Device

Similar to examples 1 and 2 but using a Q Sartobind ion exchange device.

Example 9

SARTOBIND® Phenyl Membrane Device

Similar to example 3 but using a SARTOBIND® Phenyl membrane device.

Example 10

Ion Exchange Monolith Device

Similar to examples 1 and 2 but using an ion exchange monolith device.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A process for purification comprising:
    contacting a mixture containing a target substance and one or more contaminants to a chromatography matrix such that the target substance is bound to the chromatography matrix;
    washing the bound target substance in a single step with a wash buffer that contains a combination of a lyotropic agent or an organic solvent, a detergent and a salt component;
    desorbing the bound target substance from the chromatography matrix with an eluent; and
    collecting the desorbed target substance wherein the concentration of the one or more contaminants is reduced by 91 to 99.9%.

2. The process of claim 1, wherein the wash buffer contains the lyotropic agent, the detergent and the salt component.

3. The process of claim 1, wherein the target substance containing at least one or more contaminants is a biological sample, a cell culture, a cell extract, a cell lysate, a fermentation product, or a combination thereof.

4. The process of claim 1, wherein the target substance containing at least one or more contaminants is derived from yeast, bacteria, or cell culture.

5. The process of claim 1, wherein the target substance comprises one or more of an anionic polysaccharide, an anionic protein, a protein, a polysaccharide, an anionic molecule, a cationic molecule, or a nucleic acid.

6. The process of claim 1, wherein the one or more contaminants comprises one or more of media components, nucleic acids, endotoxins, proteins, lipids, or liposaccharides.

7. The process of claim 1, wherein the eluate contains not more than 3 endotoxin units/mg of the at least one or more contaminants.

8. The process of claim 1, wherein the eluate contains not more than 2.5 endotoxin units/mg of the at least one or more contaminants.

9. The process of claim 1, wherein the chromatography matrix is an anion exchange chromatography sorbent, a cation exchange chromatography sorbent, a hydrophobic interaction chromatography sorbent, a Cibacron Blue pseudo affinity sorbent, a mixed mode chromatography sorbent, a membrane, a monolith chromatography device or a combination thereof.

10. The process of claim 1, wherein the combination is synergetic and removes multiple contaminants during the washing.

11. The process of claim 1, wherein the lyotropic agent is urea, guanidine hydrochloride, arginine, sodium thiocyanide, or a combination thereof.

12. The process of claim 1, wherein the organic solvent is isopropanol, ethanol, glycerol, ethylene glycol, propylene glycol, or a combination thereof.

13. The process of claim 1, wherein the detergent is a non-ionic detergent, polysorbate 20, polysorbate 80, sodium dodecyl sulfate (SDS), sodium sarcosine, or a combination thereof.

14. The process of claim 1, wherein the salt is sodium chloride, potassium chloride, ammonium sulfate, sodium phosphate, or a combination thereof.

15. The process of claim 1, wherein the wash buffer comprises the organic solvent, the detergent and the salt component.

16. The process of claim 1, wherein the wash buffer contains about 2 to 30% isopropanol, about 10 to 2000 mM of salt, and about 0.01% to 1% (vol/vol) octylphenoxypolyethoxyethanol.

17. The process of claim 16, wherein the suitable pH is from pH 5-9.

18. The process of claim 1, wherein the wash buffer comprises about 1 to 8 molar urea, about 10 to 2000 mM of salt, and about 0.01 to 1% (vol/vol) octylphenoxypolyethoxyethanol.

19. The process of claim 18, wherein the pH is from pH 5-9.

20. The process of claim 1, wherein the wash buffer comprises a salt concentration which is different than the concentration of salt in the eluent.

21. The process of claim 20, wherein the wash buffer has a lower salt concentration than the concentration of salt in the eluent.

22. The process of claim 1, wherein the concentration of the one or more contaminants in the eluate is reduced by 99% or more as compared to the target substance before purification.

23. A process for purification of a target comprising:
   adsorbing a mixture containing the target and one or more contaminants to an ion exchange chromatography matrix, wherein at least one of the one or more contaminants comprises an endotoxin;
   washing the bound target with a single wash buffer which contains a synergistic combination of a lyotropic agent or an organic solvent, a detergent and a salt component;
   desorbing the bound target from the chromatography matrix; and
   collecting the desorbed target wherein the level of endotoxin is less than or equal to 3 endotoxin units/mg of target.

24. The process of claim 23, wherein the amount of the one or more contaminants in the desorbed target is reduced by 91% to 99.9%.

25. The process of claim 23, wherein the target is a protein and the wash buffer contains the organic solvent, the detergent and the salt component.

26. A process for purification of a target from a mixture containing targets and contaminants that include endotoxin, wherein the process comprises:
   adsorbing the target to an ion exchange chromatography matrix;
   washing the bound target with a first wash buffer and a second wash buffer, wherein the first wash buffer contains a lyotropic agent and the second wash buffer contains an organic solvent, and each of the first and second wash buffers further contains a detergent and a salt;
   desorbing the bound target from the chromatography matrix; and
   collecting the desorbed target wherein the level of endotoxin is no more than 3 endotoxin units/mg of target.

27. The process of claim 26, wherein the target is a polysaccharide.

28. The process of claim 26, wherein the target is a protein.

29. The process of claim 26, wherein the lyotropic agent is urea, guanidine hydrochloride, arginine, sodium thiocyanide, or a combination thereof.

30. The process of claim 26, wherein the organic solvent is isopropanol, ethanol, glycerol, ethylene glycol, propylene glycol, or a combination thereof.

31. The process of claim 26, wherein the detergent is a non-ionic detergent, polysorbate 20, polysorbate 80, sodium dodecyl sulfate, sodium sarcosine, or a combination thereof.

32. The process of claim 26, wherein the salt is sodium chloride, potassium chloride, ammonium sulfate, sodium phosphate, or a combination thereof.

33. The process of claim 26, wherein the pH of each of each of the first and second wash buffers is from pH 5-9.

34. The process of claim 26, wherein washing comprises sequential washes with the first and second wash buffers in any order.

35. The process of claim 26, wherein the level of endotoxin in the desorbed target is no more than 2.5 endotoxin units/mg of target.

36. The process of claim 26, wherein the amount of the contaminants present in the desorbed target is reduced by 91% to 99.9% as compared to the amount of contaminants in the mixture.

* * * * *